United States Patent
Ralston et al.

(10) Patent No.: US 10,143,219 B2
(45) Date of Patent: Dec. 4, 2018

(54) NUTRITIONAL SUPPLEMENT/FEED FORMULA AND METHODS OF USE THEREOF TO REDUCE DEVELOPMENT OF OSTEOCHONDROSIS DISSECANS (OCD) LESIONS

(71) Applicants: RUTGERS, THE STATE UNIVERSITY OF NEW JERSEY, New Brunswick, NJ (US); THE TRUSTEES OF PRINCETON UNIVERSITY, Princeton, NJ (US)

(72) Inventors: Sarah Ralston, Howell, NJ (US); Istvan Pelczer, Princeton, NJ (US)

(73) Assignees: Rutgers, The State University of New Jersey, New Brunswick, NJ (US); The Trustees of Princeton University, Princeton, NJ (US)

( * ) Notice: Subject to any disclaimer, the term of this patent is extended or adjusted under 35 U.S.C. 154(b) by 286 days.

(21) Appl. No.: 14/773,707

(22) PCT Filed: Mar. 6, 2014

(86) PCT No.: PCT/US2014/021230
§ 371 (c)(1),
(2) Date: Sep. 8, 2015

(87) PCT Pub. No.: WO2014/138407
PCT Pub. Date: Sep. 12, 2014

(65) Prior Publication Data
US 2016/0015057 A1    Jan. 21, 2016

Related U.S. Application Data

(60) Provisional application No. 61/773,444, filed on Mar. 6, 2013.

(51) Int. Cl.
| | | |
|---|---|---|
| A61K 31/197 | (2006.01) |
| A61K 31/202 | (2006.01) |
| A23K 1/18 | (2006.01) |
| A61K 31/355 | (2006.01) |
| A61K 31/375 | (2006.01) |
| A61K 31/381 | (2006.01) |
| A61K 31/405 | (2006.01) |
| A61K 31/51 | (2006.01) |
| A61K 31/7008 | (2006.01) |
| A61K 31/7048 | (2006.01) |
| A61K 31/714 | (2006.01) |
| A61K 31/737 | (2006.01) |
| A61K 33/06 | (2006.01) |
| A61K 33/30 | (2006.01) |
| A61K 33/34 | (2006.01) |
| A61K 33/42 | (2006.01) |
| A61K 45/06 | (2006.01) |

(Continued)

(52) U.S. Cl.
CPC .......... *A23K 1/1806* (2013.01); *A23K 20/111* (2016.05); *A23K 20/116* (2016.05); *A23K 20/121* (2016.05); *A23K 20/142* (2016.05); *A23K 20/158* (2016.05); *A23K 20/163* (2016.05); *A23K 20/174* (2016.05); *A23K 20/24* (2016.05); *A23K 20/26* (2016.05); *A23K 20/30* (2016.05); *A23K 50/20* (2016.05); *A23K 50/60* (2016.05); *A61K 31/197* (2013.01); *A61K 31/202* (2013.01); *A61K 31/355* (2013.01); *A61K 31/375* (2013.01); *A61K 31/381* (2013.01); *A61K 31/405* (2013.01); *A61K 31/51* (2013.01); *A61K 31/7008* (2013.01); *A61K 31/7048* (2013.01); *A61K 31/714* (2013.01); *A61K 31/737* (2013.01); *A61K 33/06* (2013.01); *A61K 33/30* (2013.01); *A61K 33/34* (2013.01); *A61K 33/42* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | | | |
|---|---|---|---|---|---|
| 4,702,923 A | * | 10/1987 | Tokumaru | .............. | A23C 9/127 426/34 |
| 5,043,328 A | * | 8/1991 | Weithmann | ............ | A61K 31/20 514/440 |

(Continued)

FOREIGN PATENT DOCUMENTS

EP    1980500 A1    10/2008

OTHER PUBLICATIONS

Rutgers New Jersey Agricultural Experiment Station. "Report on Major Programs: Equine Science Center Research" Oct. 15, 2012, pp. 1-46.

(Continued)

*Primary Examiner* — Alma Pipic
(74) *Attorney, Agent, or Firm* — Kathleen D. Rigaut; Dann, Dorfman, Herrell & Skillman

(57) ABSTRACT

A novel dietary supplement and nutritional aid and methods for the manufacture and administration of the same are disclosed for the inhibition of OCD in afflicted animals, particularly horses. The present invention relates generally to a feed composition and methods of use thereof for reducing the development of Osteochondrosis Dissecans (OCD) lesions in predisposed young animals, particularly horses. More specifically the invention provides a nutritional formula that targets the metabolic deficiencies identified as being correlated with development of OCD.

2 Claims, 3 Drawing Sheets

(51) Int. Cl.

| | | |
|---|---|---|
| A23K 20/174 | (2016.01) | |
| A23K 20/111 | (2016.01) | |
| A23K 20/116 | (2016.01) | |
| A23K 20/121 | (2016.01) | |
| A23K 20/142 | (2016.01) | |
| A23K 20/158 | (2016.01) | |
| A23K 20/163 | (2016.01) | |
| A23K 20/24 | (2016.01) | |
| A23K 20/26 | (2016.01) | |
| A23K 20/20 | (2016.01) | |
| A23K 50/20 | (2016.01) | |
| A23K 50/60 | (2016.01) | |

(56) References Cited

U.S. PATENT DOCUMENTS

| | | | | |
|---|---|---|---|---|
| 6,632,804 B2* | 10/2003 | Ekanayake | ........... | A61K 31/375 514/62 |
| 7,601,373 B2 | 10/2009 | McCormick | | |
| 2001/0020007 A1* | 9/2001 | Wiss | ........ | A23L 29/30 514/5.9 |
| 2001/0031744 A1* | 10/2001 | Kosbab | ........ | A61K 36/15 514/54 |
| 2008/0031869 A1* | 2/2008 | Fontaine | ........ | A61K 31/201 424/94.65 |
| 2010/0034901 A1 | 2/2010 | Johnson, Jr. | | |
| 2010/0323081 A1* | 12/2010 | Katsumata | ........ | A23L 2/56 426/590 |
| 2011/0044944 A1* | 2/2011 | Theoharides | ........ | A61K 31/225 424/85.4 |

OTHER PUBLICATIONS

Ralston. "Nutritional Requirements of Horses" Merck Veterinary Manual, Jul. 2011, pp. 1-14.
50th Maryland Nutrition Conference for Feed Manufacturers, Proceedings, Mar. 27-18, 2003. pp. 1-212.
Ralston "Nutritional Supplement and Feed Compositions to Prevent Development of Osteochondrosis Dissecans Lesions in Genetically Predisposed Foals" Rutgers Invention Disclosure, Apr. 25, 2014.
Goggs, R., et al. "Nutraceutical Therapies for Degenerative Joint Diseases: A Critical Review", Critical Reviews in Food Science and Nutrition, 2005, 45, 3, ProQuest Hospital Collection, p. 145.
MVP Newsletter, Feeding and Nutrition Information—Joint Support, Sep. 2012, Med Vet Pharmaceuticals, p. 2.
Canine Food—Jan. 2005, www.hillspet.co.id/en-id/products/pd-canine-jd-dry.html.
Kitten Health Food, Apr. 2008.

* cited by examiner

NUTRITIONAL SUPPLEMENT/FEED FORMULA AND METHODS OF USE THEREOF TO REDUCE DEVELOPMENT OF OSTEOCHONDROSIS DISSECANS (OCD) LESIONS

The present application is § 371 application of PCT/US2014/021230 filed 6 Mar. 2014 which claims priority to U.S. Provisional Application 61/773,444 filed 6 Mar. 2013, the entire disclosure of each being incorporated by reference herein.

FIELD OF THE INVENTION

The present invention relates generally to a feed composition and methods of use thereof for reducing the development of Osteochondrosis Dissecans (OCD) lesions in predisposed young animals, particularly horses. More specifically the invention provides a nutritional formula that targets the metabolic deficiencies identified as being correlated with development of OCD.

BACKGROUND OF THE INVENTION

Several publications and patent documents are cited throughout the specification in order to describe the state of the art to which this invention pertains. Each of these citations is incorporated herein by reference as though set forth in full.

Osteochondritis dissecans, often abbreviated to OCD or OD, is a joint disorder in which defects form in the articular cartilage and the underlying subchondral bone. OCD is caused by blood deprivation in the subchondral bone. This loss of blood flow causes the subchondral bone to die in a process called avascular necrosis. The bone is then reabsorbed by the body, leaving the articular cartilage it supported prone to damage. The result is fragmentation (dissection) of both cartilage and bone, and the free movement of these osteochondral fragments within the joint space, causing pain and further damage. Many species are affected by OCD, including horses, dogs, pigs, horses, cattle, chicken, turkeys and humans, Osteochondritis Dissecans (OCD) is a common problem in many breeds of horses, including Thoroughbreds. In some breeds (notably Standardbreds, Hanoverians, Swedish Warmbloods) a strong genetic predisposition has been documented. Though nutritional imbalances are known to contribute to the development of OCD, in recent years emphasis has been placed on understanding the metabolic and genetic contributions to the disease. Nuclear Magnetic Resonance (NMR) Spectroscopy and Metabonomics have been identified as tools that are useful in this research.

Osteochondrosis dissecans lesions are a significant economic problem in the equine industry, affecting 20-30% of young Standardbred, Thoroughbred and Hanoverian horses in several surveys. Though lesions can be surgically corrected, the surgery is expensive and affected horses bring lower prices than horses without lesions. It is well recognized to be a heritable predisposition. Clearly a need exists to reduce the incidence of this condition, and/or for inhibiting its occurrence in predisposed animals.

SUMMARY OF THE INVENTION

The present inventors have identified the metabolic pathways impacted by the development of OCD and have assembled serum profiles from affected horses associated with the development of lesions. In accordance with the present invention, feed compositions and methods of use thereof are disclosed which are useful for mitigating these metabolic defects thereby inhibiting or prevent the development of OCD in predisposed young horses.

With this invention, a novel dietary supplement that is specifically formulated to treat and/or prevent OCD is provided. Through the periodic administration of this dietary supplement to horses or other animals in accordance with methods taught by the present invention, the development of OCD is effectively reduced and/or inhibited in such horses. As will rapidly become apparent to those skilled in the art, the dietary supplement of the present invention is much more than the sum of its ingredients, with the combination of ingredients yielding a synergistic result substantially more efficacious than if each of the ingredients acting by itself or in concert with only a few others were provided to horses.

DETAILED DESCRIPTION OF THE INVENTION

Figure 1:
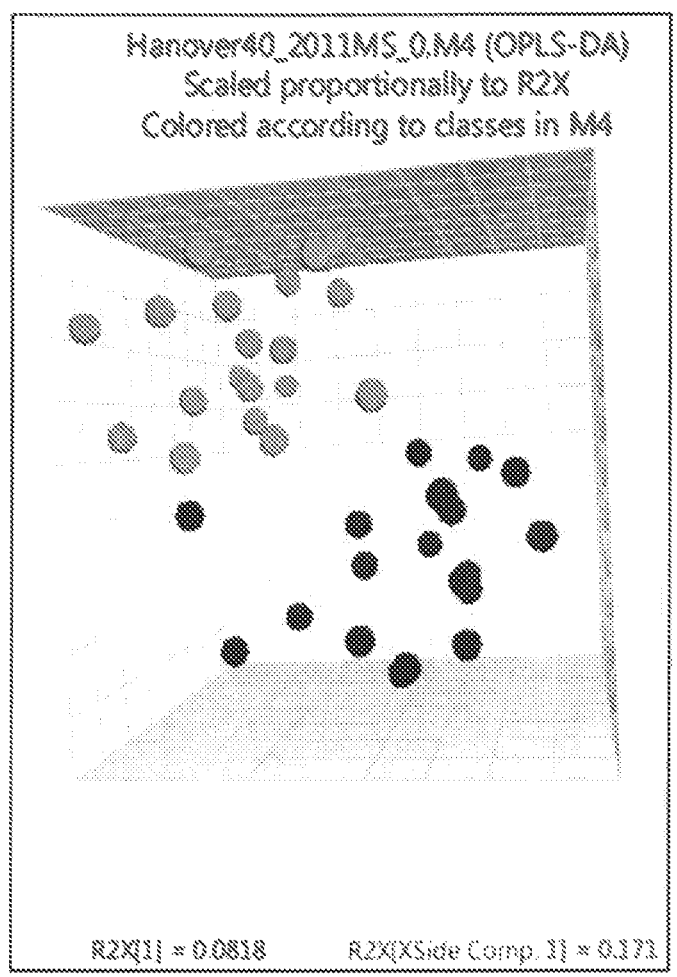
FIG. 1 shows scores plot of orthogonal partial least squares discriminant analysis of serum NMR data from yearling Standard bred horses with (green dots) and without (blue dots) OCD. The clusters reflect the distinct and unique metabolic profiles of genetically predisposed versus unaffected young horses of the same age and fed the same rations.

A novel combination of nutrients in a supplement designed to mitigate the metabolic defects discovered to be highly correlated ($P<0.001$) with the development of osteochondrosis Dissecans (OCD) lesions in the articular cartilage of young horses or other animals is disclosed.

Nuclear magnetic resonance (NMR) metabonomic studies of over 200 yearling and nursing Standardbreds pair matched for sire and similarly bred dams, fed the same ration and in the same environment for their entire lives, in 5 different studies were conducted in 2007-2012.

In a prospective metabonomic study serum samples taken from 18 nursing foals whose dams had produced OCD in the past predicted the development of OCD with >85% accuracy. In all studies there were consistent metabolic differences in metabolites between affected and control horses that point toward specific metabolic defects that could potentially be amenable to nutritional amelioration.

It is well documented that OCD can be caused by major mineral and energy imbalances in the ration of young horses (Savage et al, 1993 a, b) and that there is a hereditary component in certain breeds (Hoppe and Phillipson, 1985, Phillipson et al, 1993, Piermattei et al, 2003), but no metabolic correlations, other than relative insulin resistance (Ralston, 1996), have been identified.

The specific metabolic differences identified by the present inventor are associated with differences in amino acid utilization, vitamins and lipoprotein oxidation that give rise to defects in the TCA cycle and mitochondrial beta-oxidation which are amenable to nutritional manipulation. To date, no other OCD preventative supplement has been developed based on these observable metabolic differences between normal and OCD disposed horses.

The proposed nutritional formula, whether provided as a separate supplement, feed or complete feed, to mares in their late pregnancy and early lactation and weanling and yearling horses, would provide per kilogram body weight basis daily:
0.001 to 0.05 gm ascorbic acid or dihydroascorbate derivatives, more preferably, 0.005 gm;
0.005 to 0.05 mg Thiamine, more preferably, 0.01 mg;
0.007 to 0.05 gm of Omega-3 fatty acids from any source, more preferably, 0.01 gm;
0.004 to 0.01 gm tryptophan from any source, more preferably, 0.07 gm;
10-30 mg Glucosamine hydrochloride, more preferably 20 mg;
3 to 10 mg chondroitin sulfate, more preferably, 5 mg;
Other fillers may also be provided as necessary.
Optional Ingredients include one or more of:
1 to 25 iu vitamin E;
0.01 to 0.1 gm calcium;
0.01 to 0.1 gm phosphorus;
0.01 to 0.02 mg copper;
0.01 to 0.08 mg, zinc, preferably 0.02 to 0.04 mg;
10 to 20 mg Panthothenic acid, preferably, 15 mg;
40 to 100 mg Vitamin B-12, preferably 70 mg;
3 to 9 grams Hesperdin Complex, more preferably 6 grams;
5-10 grams of Lipoic Acid, preferably, 7 grams.
An exemplary formula consists of provision PER Kg BW daily:
0.005 gm ascorbic acid or dihydroascorbate derivatives
0.01 mg Thiamine
0.01 gm of Omega-3 fatty acids from any source,
0.07 gm tryptophan from any source
20 mg Glucosamine hydrochloride
5 mg chondroitin sulfate
Other fillers may also be provided as necessary.
Optional ingredients include one or more, or all of the components listed below:
15 iu vitamin E
0.1 gm calcium
0.05 gm phosphorus
0.015 mg copper
0.03 mg zinc
15 mg Panthothenic acid
70 mg Vitamin B-12
6 grams Hesperdin Complex
7 grams of Lipoic Acid The following definitions are provided to facilitate an understanding of the present invention.

The term "carbohydrate" as used herein includes polysaccharides (e.g., starches and dextrins) and sugars (e.g. sucrose, lactose, maltose, glucose, and fructose) that are metabolized for energy when hydrolyzed. Examples of carbohydrates suitable for inclusion in the compositions disclosed herein include, but are not limited to, corn, grain sorghum, wheat, barley, and rice.

The term "antioxidant" means a substance that is capable of reacting with free radicals and neutralizing them. Illustrative examples of such substances include beta-carotene, selenium, coenzyme Q10 (ubiquinone), lutein, tocotrienols, soy isoflavones, S-adenosylmethionine, glutathione, taurine, N-acetylcysteine, vitamin E, vitamin C, lipoic acid and L-carnitine. Examples of foods containing useful levels of one or more antioxidants include but are not limited to ginkgo biloba, green tea, broccoli, citrus pulp, grape pomace, tomato pomace, carrot spinach, and a wide variety of fruit meals and vegetable meals. It will be understood by one of skill in the art that while units of antioxidants may be provided herein as "ppm" or "mg/kg" feed or body weight, appropriate amounts of antioxidants may also be provided as "IU/kg feed or body weight" where appropriate and customary for a given antioxidant such as, e.g., Vitamin E The terms "beneficial change" in gene expression, or gene expression may be "beneficially altered" and like terms refer to a modification in gene expression (e.g., up or down regulation of mRNA levels) such that levels of proteins encoded by the genes may be correspondingly modified such that an associated biological pathway may be more likely to function normally and with less tendency to reflect pathological changes in the pathway that, e.g., may be typical of a normal or OCD affected animal. Generally, beneficial changes in gene expression relate to improved health and/or reduced propensity for disease in an animal. As used herein, measuring differences in gene expression "levels" and like terms refer to, e.g., characterizing whether expression of a gene is up or down regulated in an animal compared to a control level.

An "improvement" or an "enhancement" in a characteristic or biological pathway refers to a modification in said characteristic or biological pathway such that there is a tendency for the characteristic or pathway to appear and/or function normally and with less tendency to reflect pathological changes in the characteristic or pathway that, e.g., may be typical of a normal animal.

As used herein, methods to "treat" an animal suffering from a disease or disorder is also meant to encompass methods to inhibit development and/or to ameliorate the disease or disorder as well.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim, an in the latter instance, impurities ordinarily associated with the specified material(s). The term "consisting essentially of" limits the scope of a claim to the specified elements, steps or materials and those that do not materially affect the basic and novel characteristic(s) of the claimed subject matter.

The following example is provided to illustrate certain embodiments of the invention. It is not intended to limit the invention in any way.

EXAMPLE I

Nuclear magnetic resonance (NMR) metabonomic studies of over 200 yearling Standardbreds pair matched for sire and similarly bred dams, fed the same ration and in the same environment for their entire lives, in 5 different studies were conducted in 2007-2012. The only difference between the paired animals in each study was that 1of the pair had no evidence of OCD (either clinically or on radiographic evaluation) and the other had had surgery to correct OCD lesion 1 to 12 months prior to samples taken. In a prospective metabonomic study, serum samples taken from 18 nursing foals whose dams had produced OCD in the past predicted the development of OCD with >85% accuracy. In all studies there were consistent metabolic differences in metabolites between affected and control horses. See FIG. 1

Figure 2:
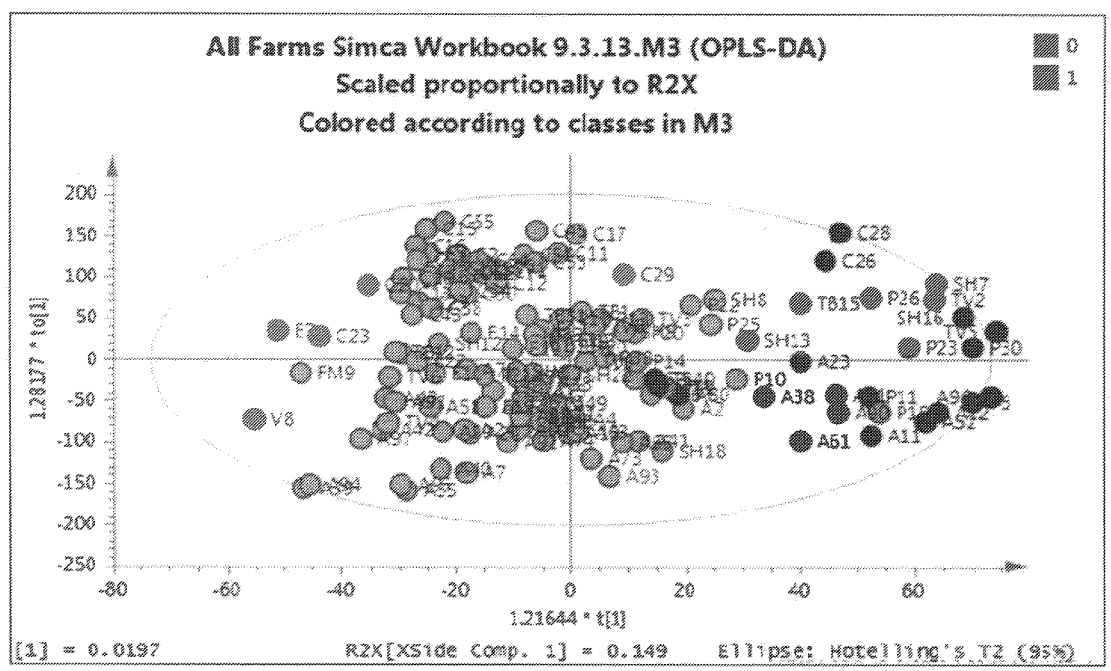
FIG. 2 shows discriminant analysis of all Australian Thoroughbred Yearling horses tested (n=220) Color coding is the same as in FIG. 1
Figure 3:
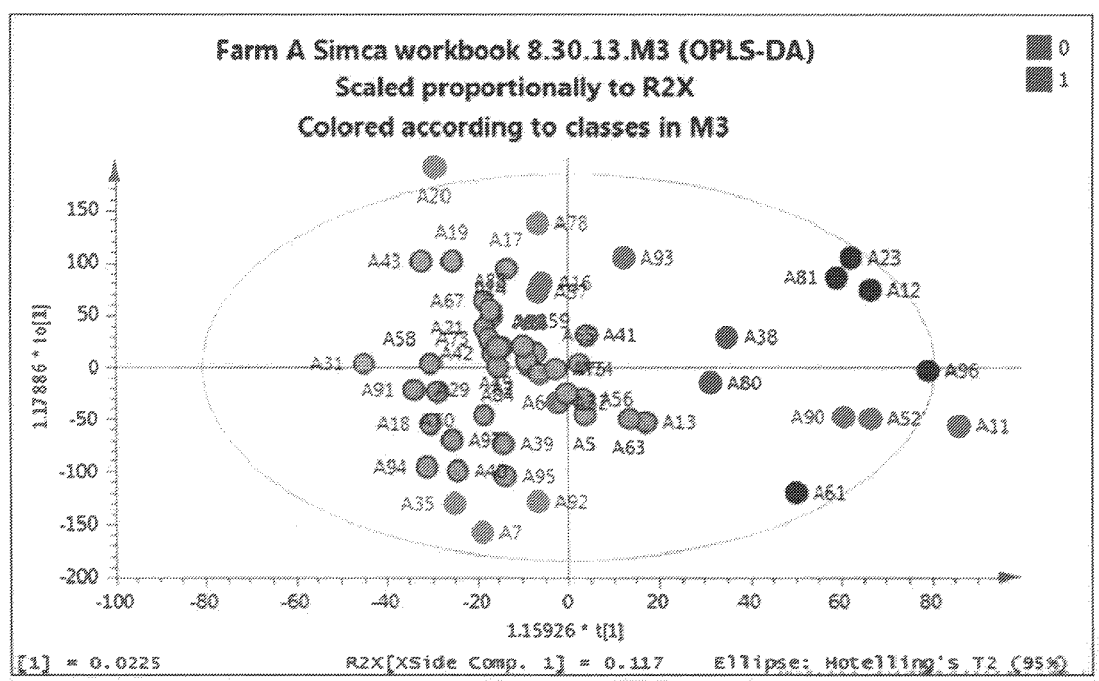
FIG. 3 shows discriminant analysis of all Yearling Thoroughbred horses tested on Farm A. Color coding is the same as in FIGS. 1 and 2

We performed additional studies on a total of 220 yearlings, representing 13 stallions and had an overall incidence of OCD of 21%±7. However 5 sires had >25% OCD in their offspring, whereas 3 had <15% OCD, suggesting a possible genetic influence. The metabonomic analyses revealed a clear metabolic separation between OCD and Non-OCD-affected horses, both across the entire sample and within individual farms (FIGS. 2 and 3). As with Standardbreds, metabolites of significance to the metabolic separation are located in the amino acid, sugar and lipid regions of the NMR spectra, suggesting defects in amino acid, anti-oxidant and fatty acid pathways that may be amenable nutritional correction The dietary supplement of the present invention should provide benefit to animals afflicted with OCD or at risk of developing this disorder. In one approach, the formulation comprises a pelleted feed supplement designed to be top-dressed at the rate of 1 kg per horse per day with the specified nutrients with in the midrange of the concentrations specified above.

Based on prior studies, we hypothesize that the metabolic "defects" in predisposed foals, as reflected in altered metabolic profile based on NMR spectra, could potentially be circumvented with the inventive nutritional supplement described herein thereby reducing the development of lesions and altering the metabolic profile to coincide with that of non-affected animals.

Therapeutic Results

All horses will be evaluated radiographically for OCD lesions 10 to 24 months on the supplement. Blood samples will be obtained from all horses at weaning and at 18 to 24 months for NMR analysis. The NMR spectra will be compared between affected and non-affected horses and between dietary treatments. It is anticipated that there will be significantly fewer OCD affected horses in the supplemented group and that the NMR spectra of the supplemented foals will coincide more closely to the unaffected foals in both groups than those with OCD.

All testing of the product will be pre-approved by the Animal Care and Use Committee of Rutgers, the State University of New Jersey.

The dietary supplement of the present invention does not interfere with the proper digestion of foodstuffs while it is treating and/or preventing OCD. It consists entirely of safe and natural ingredients rather than drugs. The dietary supplement of the present invention is orally administrable in either liquid or solid form, thereby making its dispensation a simple matter. It can also be packaged in single doses to make its administration as convenient as is possible.

The dietary supplement of the present invention will be stabilized to have a long shelf life, and requires no special care to be provided by the user throughout its shelf life prior to usage. The dietary supplement of the present invention is also inexpensive relative to previously known OCD treatments, thereby enhancing its market appeal and affording it the broadest possible market. Finally, all of the aforesaid advantages and objectives of the dietary supplement of the present invention and its method of administration are achieved without incurring any substantial relative disadvantage.

Although the foregoing description of the dietary supplement of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A dietary supplement for use in inhibiting or reducing the occurrence of osteochondrosis dissecans (OCD) in animals, consisting of:
 0.005 gm ascorbic acid or dihydroascorbate derivatives,
 0.01 mg thiamine,
 0.01 gm of omega-3 fatty acids from any source,
 0.07 gm tryptophan from any source,
 20 mg glucosamine hydrochloride,
 5 mg chondroitin sulfate,
 15 iu vitamin E,
 0.1 gm calcium,
 0.05 gm phosphorus,
 0.015 mg copper,
 0.03 mg zinc,
 15 mg pantothenic acid,
 70 mg vitamin B-12,
 6 grams hesperidin complex, and
 7 grams of lipoic acid, and optionally at least one filler.

2. A method for ameliorating the symptoms of OCD in horses, comprising administration of an effective amount of a dietary supplement of claim 1 to a horse in need thereof, said dietary supplement being administered on a per kilogram body weight basis daily, wherein administration of said supplement is effective to reduce or inhibit the formation of OCD lesions.

\* \* \* \* \*